US009836793B2

(12) United States Patent
Busque et al.

(10) Patent No.: US 9,836,793 B2
(45) Date of Patent: Dec. 5, 2017

(54) INSURANCE PROCESSING SYSTEM AND METHOD USING MOBILE DEVICES FOR PROOF OF OWNERSHIP

(75) Inventors: Kevin J. Busque, Manchester, CT (US); Andrew J. Amigo, Gloucester, MA (US); Richard M. Borden, West Hartford, CT (US); David F. Peak, Avon, CT (US); Eugene J. Walters, Avon, CT (US)

(73) Assignee: HARTFORD FIRE INSURANCE COMPANY, Hartford, CT (US)

( * ) Notice: Subject to any disclaimer, the term of this patent is extended or adjusted under 35 U.S.C. 154(b) by 416 days.

(21) Appl. No.: 12/877,784

(22) Filed: Sep. 8, 2010

(65) Prior Publication Data

US 2011/0161117 A1 Jun. 30, 2011

Related U.S. Application Data

(63) Continuation of application No. 12/754,189, filed on Apr. 5, 2010, now Pat. No. 9,558,520.

(60) Provisional application No. 61/291,501.

(51) Int. Cl.
*G06Q 40/00* (2012.01)
*G06Q 40/08* (2012.01)
(Continued)

(52) U.S. Cl.
CPC ............ *G06Q 40/08* (2013.01); *G06F 19/323* (2013.01); *G06F 19/3418* (2013.01);
(Continued)

(58) Field of Classification Search
CPC ..................................................... G06Q 40/08
(Continued)

(56) References Cited

U.S. PATENT DOCUMENTS 5,451,998 A * 9/1995 Hamrick ..................... 725/60
7,653,702 B2 * 1/2010 Miner ......................... 709/217
(Continued)

OTHER PUBLICATIONS

"OiiNOW Online Insurance Inventory: Full Subscription Benefits", OiiNOW Online Insurance Home Inventory Software System, copyright 2005-2006, retrieved date Sep. 8, 2010 2:51PM, download from the Internet, http://www.insurance-inventory.com/getpro_insurance_inventory.asp, 1 pg.
(Continued)

*Primary Examiner* — Eric T Wong
(74) *Attorney, Agent, or Firm* — Howard IP Law Group, PC

(57) ABSTRACT

Systems, methods and apparatus for creating, analyzing and updating a property inventory are disclosed which include receiving, from a user operating a mobile device, a request to add a new item of property to an insurance inventory associated with an insurance policy, the request including information identifying the new item, at least a first image of the new item, and information identifying a location of the new item. An insurance inventory system is operated to add the new item to an insurance inventory associated with the insurance policy, the updating including computing a total current value of the insurance inventory including the new item. A coverage engine is operated to compare coverage limits associated with the insurance policy to the total current value of the insurance inventory to determine if the total current value is within a coverage limit of the insurance policy. A response is transmitted to the user based on the determination.

23 Claims, 8 Drawing Sheets

(51) Int. Cl.
*G06F 19/00* (2011.01)
*G06Q 10/06* (2012.01)
*G06Q 10/10* (2012.01)
*G06Q 50/22* (2012.01)
*G06Q 50/24* (2012.01)
*G06Q 20/32* (2012.01)

(52) U.S. Cl.
CPC ......... *G06F 19/366* (2013.01); *G06Q 10/067* (2013.01); *G06Q 10/10* (2013.01); *G06Q 20/3223* (2013.01); *G06Q 20/3278* (2013.01); *G06Q 50/22* (2013.01); *G06Q 50/24* (2013.01)

(58) Field of Classification Search
USPC ............................................................ 705/4
See application file for complete search history.

(56) References Cited

U.S. PATENT DOCUMENTS

| | | | |
|---|---|---|---|
| 7,729,930 B1* | 6/2010 | Bohanek | 705/4 |
| 7,899,823 B1* | 3/2011 | Trandal et al. | 707/736 |
| 7,941,330 B1* | 5/2011 | Buentello et al. | 705/4 |
| 8,041,636 B1* | 10/2011 | Hunter et al. | 705/40 |
| 2004/0000586 A1* | 1/2004 | White | 235/385 |
| 2006/0178902 A1* | 8/2006 | Vicars et al. | 705/1 |
| 2006/0282342 A1* | 12/2006 | Chapman | 705/28 |
| 2009/0171822 A1* | 7/2009 | Meadow et al. | 705/30 |
| 2010/0088123 A1* | 4/2010 | McCall et al. | 705/4 |

OTHER PUBLICATIONS

"OiiNOW Home Inventory", OiiNOW Online Insurance Home Inventory Software System, retrieved date Sep. 8, 2010 2:52PM, download from the Internet, http://www.insurance-inventory.com/default.asp, 3pgs.

"Know your Stuff", Ezasset, retrieved date Sep. 8, 2010 2:52 PM, download from the Internet, http://ezasset.appspot.com/viewOnlyNo Login.do?page=front_kys&br . . . , 1pg.

"The Inventory Insurance Plan", retrieved date Sep. 8, 2010 2:53 PM, download from the Internet, http://www.inventoryinsuranceplan.com/usa/default.htm, 1pg.

* cited by examiner

| Policy # 802 | Type 804 | Limits 806 | Current Property Value 808 | Deductible 810 | Alarm? 812 |
|---|---|---|---|---|---|
| P12323 | Personal | $10,000 / ---- | $12,000 | $500 | Yes |
| P12324 | Personal | $5,000 / ---- | $4,000 | $500 | No |
| P12326 | Personal | $10,000 / ---- | ---- | $500 | ---- |

FIG. 8

| Cust. Id 902 | Policy # 904 | Item 906 | Serial No. 908 | Photo 910 | Capture Data 912 | Date Acquired 914 | Purchase Price 916 | Replacement Price 918 | Estimated Value 920 |
|---|---|---|---|---|---|---|---|---|---|
| C1232 | P12323 | Sony Bravia TV (36") | Sxxxxxx | xx.jpg, xy.jpg | geoxxx, date/time | 12/5/2009 | $2,000 | $2,100 | $1,000 |
| | | Trek Madone | Syyyyy | xz.gif, zx.gif | geoxxy, date/time | 10/1/2008 | $6,000 | $6,500 | $5,000 |
| | | Tiffany Diamond Studs (2ct) | n/a | n/a | geoxyy, date/time | 5/1/2007 | $3,500 | $6,000 | $6,000 |

FIG. 9

INSURANCE PROCESSING SYSTEM AND METHOD USING MOBILE DEVICES FOR PROOF OF OWNERSHIP

CROSS REFERENCE TO RELATED APPLICATIONS

The present application is based on, and claims benefit and priority of, U.S. Provisional Patent Application Ser. No. 61/291,501 filed on Dec. 31, 2009, and is a continuation of U.S. patent application Ser. No. 12/754,189, filed on Apr. 5, 2010, the contents of each of which are incorporated herein in their entirety for all purposes.

FIELD

Embodiments relate to insurance processing systems and methods. More particularly, embodiments relate to insurance processing using mobile devices to create property inventories, establish proof of ownership and analyze and update insurance coverage.

BACKGROUND

Many types of insurance coverage, such as those for personal or commercial property, have coverage terms and conditions in which the insurer will reimburse the insured for damage or loss to personal property items (in the case of personal lines insurance policies) or for damage or loss to commercial property items such as inventory or equipment (in the case of commercial lines policies). For example, if an item of personal property is stolen or damaged, many insurance policies may reimburse the insured so that the insured may obtain a suitable replacement. Similar coverage is provided for businesses. For example, a retailer may carry a commercial lines policy which covers the retailer's inventory in the case of loss or damage. Often, however, it can be difficult for an insurer to verify that an item of property was, in fact, owned by the insured. In the case of businesses, such as retailers, it is difficult to verify what items were actually in the retailer's inventory at the time of a loss, as inventories change on a daily basis.

Further, many losses arise from events such as fires or floods. In such situations, it can be difficult for an insured to remember all of the items that may have been lost or damaged. It is also difficult to locate receipts, or otherwise locate evidence of ownership or value. It would be desirable to provide systems and methods for insurance policy holders to create and maintain an inventory of personal property. It would further be desirable to allow the use of such an inventory to document claims in the event of a loss.

Insurance policies have coverage limits and exclusions. For example, a homeowner policy may cover up to $100,000 of personal property items (a "coverage limit") but will not cover fine art (an "exclusion"). Insurance policy holders often do not know if the value of their personal property exceeds these limits or what items are excluded from coverage. It would be desirable to provide systems and methods to alert policy holders if the value of covered items exceeds the coverage limits of an existing policy, or if an item is excluded from coverage. It would further be desirable to provide systems and methods to price and provide coverage based on the current value of property owned by an insured.

It would further be desirable to provide systems and methods which allow the creation and updating of such proof of ownership data to be collected and updated using mobile devices.

BRIEF DESCRIPTION OF THE DRAWINGS

FIG. 8 depicts a portion of a policy database table pursuant to some embodiments.

FIG. 9 depicts a portion of an inventory database table pursuant to some embodiments.

DETAILED DESCRIPTION

Figure 1:
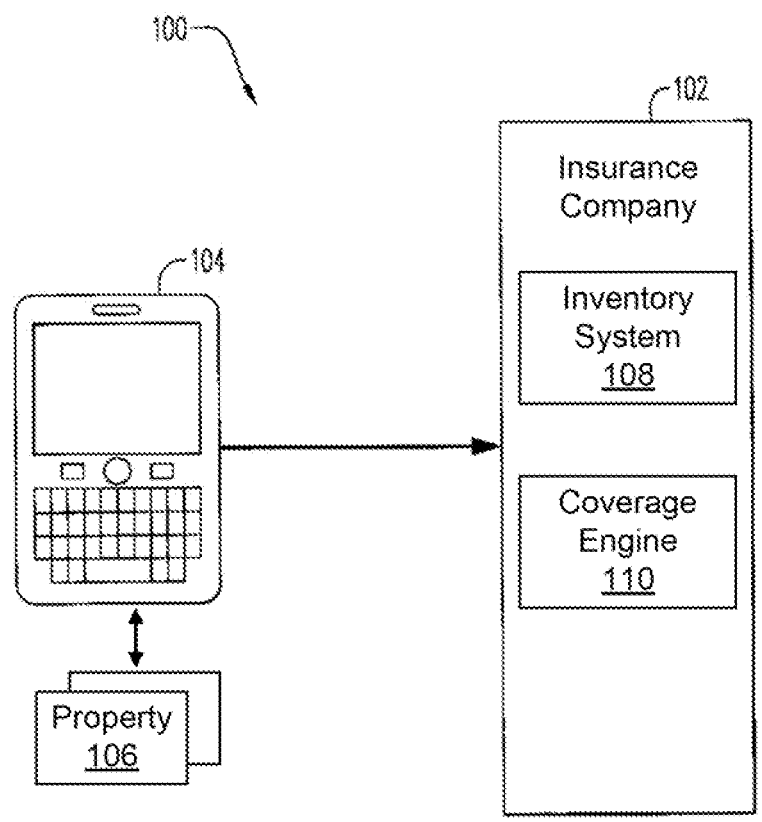
FIG. 1 illustrates a system architecture within which some embodiments may be implemented.

Embodiments of the present invention relate to systems and methods for establishing evidence or information about insured items for use in proof of insurance and for use in analyzing and/or updating coverage. Embodiments provide applications and mobile devices to allow the ready, convenient and accurate collection, submission, storage and analysis of information about items of property for insurance purposes. Embodiments relate to both personal insurance as well as commercial insurance (as well as other types of insurance where property, including inventory or equipment is insured, such as in bailment situations where an entity holds inventory or property for delivery to others).

As used herein, the term "property" or "insured property" is used to refer to items that are insured (or are to be insured or are claimed to be insured) including items of personal property (in the case of personal lines insurance) as well as items of commercial property (such as inventory, equipment, or the like, in the case of commercial lines insurance).

As used herein, the term "user" is used to refer to an operator of a mobile device (or other data collection system) which is operated to collect, report or otherwise provide information about items of property to an insurer or agent of an insurer. For example, a "user", in the case of a personal lines insurance policy, may be a homeowner, a renter, or the like, who operates a mobile device configured pursuant to the present invention to collect and provide information about items of personal property. As another example, a "user", in the case of a commercial lines insurance policy, may be an employee, owner, or other operator of one or more mobile devices (or other data collection systems) configured pursuant to the present invention to collect and provide information about items of commercial property (such as items of inventory, equipment or the like).

In some embodiments, mobile devices, such as smart phones, tablet computers, or other portable communication and computing devices, are provided with software (referred to herein as "applications," "mobile applications," or "mobile insurance applications") that allow users to easily collect, submit, store information about items of property that are (or will be) covered by one or more insurance policies. Further, embodiments allow users to be notified of situations when there is insufficient insurance coverage for an item, and, if needed, allow the user to obtain additional insurance coverage. For example, in some embodiments, users may operate mobile devices operating a mobile application to capture information about items of property. The mobile device may then be used to transmit the information to an insurance company or other entity for storage in an inventory database associated with the user. Further, in some embodiments, an analysis or evaluation of the user's inventory or each item may occur to determine if the user's insurance coverage is sufficient. In some embodiments, the user may apply for and obtain additional coverage based on the determination.

Pursuant to some embodiments, the pricing, exclusions and/or coverage limits of an insurance policy may be updated based on the current value of items in an inventory. For example, in the case of a commercial lines policy for a retailer, some embodiments allow daily, weekly or other regular updates to a policy based on the value of items owned by the retailer, which may vary as the retailer adds items to inventory and sells items from inventory. In this manner, a retailer may enjoy coverage which accurately reflects the retailer's actual inventory as well as policy pricing which varies as the inventory turns over. As another example, in the case of a personal lines insurance policy which excludes coverage for fine art, or high-value jewelry, some embodiments notify an insured that an item of property is excluded from coverage when the insured attempts to add it to a property inventory. In some embodiments, a rider to extend coverage (and to cover the excluded item) may be provided (either automatically or in response to further interaction with the insured).

The result is a system and method that provides improved information for processing claims associated with items of property, as well as a convenient and efficient method of tracking items of property. Further, embodiments allow users to maintain (and obtain) sufficient levels of insurance coverage based on the current or replacement value of the user's items of property.

Pursuant to some embodiments of the present invention, users who provide information about their items of property using features of the present invention may be entitled to reduced premiums or may qualify for other insurance-related benefits. For example, pursuant to some embodiments, a user who has provided information about items of property, and who then suffers a loss related to one of those items of property, may receive substantially immediate processing of a claim, with reduced claim processing requirements. As another example, users who use features of the present invention to prove that the user has taken certain steps to secure the property (e.g., such as by the installation of a qualified alarm system, etc.) may enjoy improved benefits, such as a reduced deductible, reduced premium, or the like. As a still further example, users may utilize features of the present invention to prove that they have taken appropriate care in maintaining or using items of property. As a specific example, a homeowner or retailer whose insurance requires that a room or product be kept at a certain minimum temperature may use the mobile insurance application to take a periodic measurement of the status of the room or item.

Features of some embodiments will now be described by reference to FIG. 1, which is a block diagram of an insurance processing system 100 pursuant to some embodiments. As shown in FIG. 1, a system 100 includes a mobile device 104 in communication with an insurance company 102. The mobile device 104 is coupled to capture or otherwise receive data and information associated with one or more items of property 106 associated with an insurance policy issued by insurance company 102. The insurance company 102 operates systems to process insurance policies based on the property data received from the mobile device 104. For example, the insurance company 102 operates systems to store and track property data on behalf of users (e.g., storing the data in an inventory system 108) as well as systems to analyze coverage based on the value or nature of items of property identified using the present invention (e.g., using a coverage engine 110). In some embodiments, the coverage engine 110 and/or the inventory system 108 may be operated or maintained by entities other than the actual insurer, such as, for example, an agent of the insurance company 102 or other service provider. For ease of exposition, however, the systems and processes herein will be described as being performed by an insurance company 102.

Pursuant to some embodiments, a mobile insurance application may be stored in, or accessible to, a memory of mobile device 104 which allows a user of the mobile device to take an inventory of items to be covered by an insurance policy issued by the insurance company 102. For example, homeowners or renters often seek insurance coverage for personal property contained within their home. Frequently, however, the insured does not have proof that they owned certain items allegedly covered by a policy, and when a loss occurs, it can be difficult to prove to an insurer that an item was actually owned by the insured. This can be particularly difficult with respect to high value items.

As another example, businesses, such as retailers, often seek insurance coverage for their inventory. A jewelry store, for example, may seek coverage for their inventory of rings and jewelry. Such coverage is typically priced and issued based on an expected level of inventory value. For example, a jewelry store that expects to stock an average of $1,000,000 of inventory will seek coverage for $1,000,000 of inventory. Often, however, the retailer may have substantially less inventory than average (such as after a successful sale, or before receipt of a new shipment) or substantially more inventory than average (such as prior to a sale, during a slow sales period, or after receipt of a new shipment). In such cases, it would be desirable to provide more accurate insurance pricing that reflects the actual current value of the inventory. Embodiments allow such a business (operating one or more mobile devices 104) to provide current inventory information to insurance company 102. The current inventory information may be used by the insurance company 102 to adjust an insurance premium or coverage limits as well as to process any claims that may relate to a loss suffered by the business.

Embodiments of the present invention allow an insured to download and interact with a mobile insurance application on their mobile device 104 which lets them create an inventory of items. The inventory may be stored in or accessible to the insurance company 102 (e.g., such as in an inventory system 108). The inventory system 108 may store a number of different items of information about each item (including, for example, a photo of the item, a photo or scan of a receipt for the item, and/or other item descriptive information). In some embodiments, geotag data and time stamp data are also associated with the item for additional proof of ownership and possession. The inventory system 108 may serve as a central repository or may be coupled to archival systems to maintain the data for use by the insurance company 102 and the user.

In some embodiments, when an insured purchases or acquires a new item for which insurance coverage is sought, the insured operates the mobile device 104 using the mobile insurance application and registers the new item. The registration may include information identifying the item (or an item type) as well as, in some embodiments, the purchase price, a purchase receipt, etc. In some embodiments, the insured may provide general information about an item, and further data may be generated or collected by the inventory system 108. For example, in some embodiments, an insured need not always provide purchase price information. Instead, the inventory system 108 may assign a default or estimated price to an item based on the descriptive information provided by the insured. In exchange for promptly providing such information, an insurance company 102 may provide benefits, such as a commitment to process any loss claims more quickly, additional replacement coverage, or the like.

In some embodiments, when a new item is added to an insured's inventory using the mobile insurance application of the present invention, an underwriting process may be invoked or triggered to analyze the insured's policy and existing inventory to determine if sufficient coverage limits are in place to fully cover the new item as well as the existing inventory. For example, in a situation where the invention is used in a personal lines situation, if an insured currently has $100,000 of personal property in her inventory, and acquires a new custom-built bicycle that is worth $10,000, the underwriting module may determine whether her existing policy is adequate to cover $110,000 of personal property in the event of a loss. If the current policy is inadequate, and an additional rider or coverage is required, embodiments allow the insured to obtain such additional coverage by interacting with the mobile insurance application on the mobile device 104. The underwriting process may also evaluate whether the item (or items) to be added are excluded by one or more policy exclusions. If so, embodiments may allow the insured to obtain additional coverage by interacting with the mobile insurance application on the mobile device 104 to obtain a rider or other extension of coverage to ensure the item(s) are adequately insured.

As another example, in a situation where the invention is used in a commercial lines situation, if an insured business has coverage for up to $1,000,000 of inventory, and takes delivery of a shipment of new inventory valued at $500,000, the underwriting module may determine whether the business' existing policy is adequate to cover the new inventory in addition to any existing inventory. If the current policy is inadequate, and an additional rider or coverage is required, embodiments allow the insured to obtain such additional coverage by interacting with the mobile application on the mobile device 104. In some embodiments, additional systems may be used to report the status of inventory. For example, in some embodiments, a retailer may transmit inventory information (including additions as well as reductions from inventory) to the insurance company 102 via an inventory management system operated by or on behalf of the retailer. In this manner, insured businesses can transmit up to date and accurate inventory information to the insurance company 102.

Pursuant to some embodiments, the entry or update of item data using the present invention may trigger or invoke an underwriting or other analysis process to analyze the user's current (or potential) insurance policy coverage to determine if there are any gaps in coverage or if the user is over insured. The analysis may also be invoked or requested by a user on an as needed basis. For example, in one illustrative embodiment, the mobile insurance application may be invoked by the user to analyze the user's current insurance coverage limits. For example, a user who is a homeowner may perform an inventory (as described above) to determine the total value of her personal property items and then request a coverage analysis pursuant to the present invention. Similar processing may be performed by commercial users.

While the present invention is described above as being for use in inventorying and analyzing items of personal or commercial property, in some embodiments features may be used to analyze coverage of real property as well. For example, in some embodiments, the user may provide details about her real property to determine if her policy is sufficient to cover her current property value. In some embodiments, this analysis may involve the use of external data from third party data sources to assess the current value of an insured's property. For example, in one embodiment, where the user wishes to analyze the coverage for a home, the user will interact with the mobile insurance application on her mobile device 104 and provide detailed information about the property. In some embodiments, if the user has registered the application, some of the property data will be retrieved from an existing policy at the insurance provider.

The user may also provide information about any upgrades or enhancements made to the property. Then, the application uses the information to obtain one or more comparative values from homes that have been sold in the user's neighborhood to generate an estimated value of the insured's property. In some embodiments, the estimate may be retrieved from existing sources, such as from the website www.zillow.com. Once an estimate of the insured's property is obtained, the mobile insurance application transmits the data (plus the value of any personal property in the insured's inventory) to the insurance company 102 for analysis.

The insurance company 102 uses the estimated value (and the value if any personal property, in an inventory, if any) and compares the value to the insured's existing policy to determine if there is a gap in coverage or if the property is over insured. In the event of a gap, a recommendation for obtaining additional coverage is generated and presented to the insured (via the mobile device 104). If the additional coverage is accepted, processing may continue to issuance of the policy with the updated coverage.

Those skilled in the art will appreciate that similar coverage analyses may be performed for a wide variety of different policy types. For example, a coverage analysis may be performed for personal property. In such embodiments, the proof of ownership system may be used to identify and analyze items owned by an insured. Third party data sources may also be used in analyzing coverage and claim information associated with personal property, as will be described further below.

The mobile device 104 may be any of a number of different types of mobile devices that allow for wireless communication and that may be carried with or by a user. For example, in some embodiments, mobile device 104 is a smart phone such as an iPhone®, a mobile device operating the Android® operating system, or other portable computing device having an ability to communicate wirelessly with a remote entity such as insurance company 102). In some embodiments, as will be described further below, additional information may be provided to the insurance company 102 using other data entry or data collection devices (such as, for example, point of sale terminals, inventory management systems, or the like).

Figure 5:
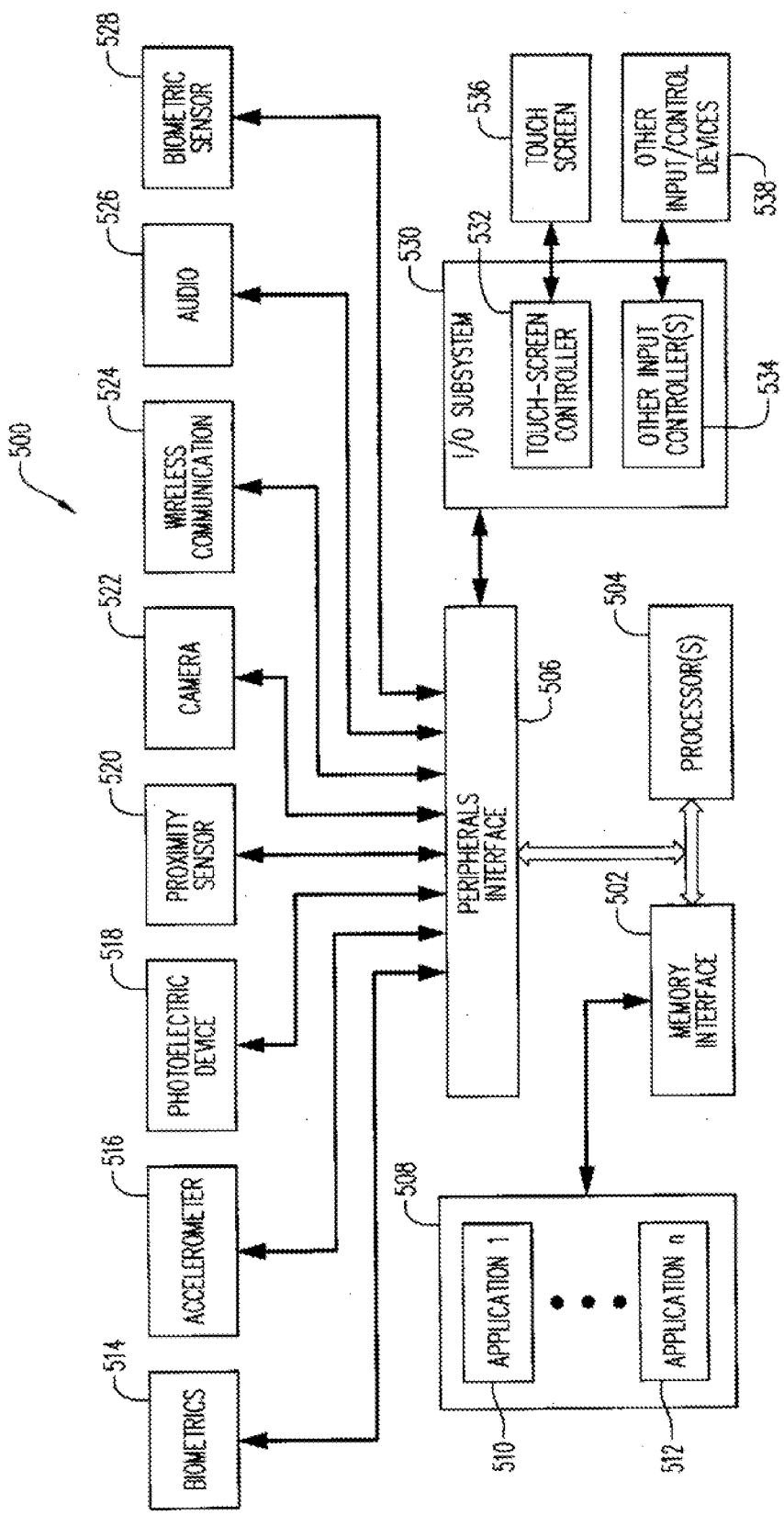
FIG. 5 is a partial functional block diagram of a mobile device and system provided in accordance with some embodiments.

Features of mobile devices 104 will be described further below in conjunction with FIGS. 5 and 6. Preferably, in some embodiments, mobile device 104 is capable of communicating with remote systems (such as insurance company 102) via wireless communication techniques (as will be described further below in conjunction with FIG. 2), and is further capable of capturing information associated with items of personal property 106. In some embodiments, the information may be captured using a camera or other image capture device, while in other embodiments, sensors (such as RFID sensors) may be used. In some embodiments, information identifying property to be added to an insurance inventory may include data that is key-entered by a user of the mobile device 102.

Pursuant to some embodiments, operation of the mobile device 104 for the collection and transmission of property related data is controlled by one or more mobile insurance applications stored in a memory of the mobile device 104.

In some embodiments, the mobile insurance application includes functionality to verify or authenticate the identity of the user so that the insurance company 102 can verify that the data was collected from the correct user. A number of different verification and authentication methods may be used in conjunction with embodiments of the present invention. For example, a user may be prompted to enter a secure password or personal identification number prior to capturing information about an item of property and transmitting the information to the insurance company 102. The verification may be controlled by the mobile insurance application or it may require communication with a verification system associated with the insurance company 102. In some embodiments, once a user is successfully authenticated or verified, the mobile insurance application may prompt the user to capture specific information about an item of property (e.g., such as taking one or more photos, scanning a bar code, entering or capturing a serial number, etc), as well as entering additional meta data associated with the item so that the information may be transmitted to the insurance company 102 and stored in an inventory system 108

Pursuant to some embodiments, data may be transmitted between devices using a wireless network. In some embodiments, some, or all, of the data may be transmitted using other network communication techniques (e.g., such as satellite communication, RFID, or the like). In some embodiments, some or all of the data transmitted between devices may be encrypted or otherwise secured to prevent intrusion.

Figure 2:
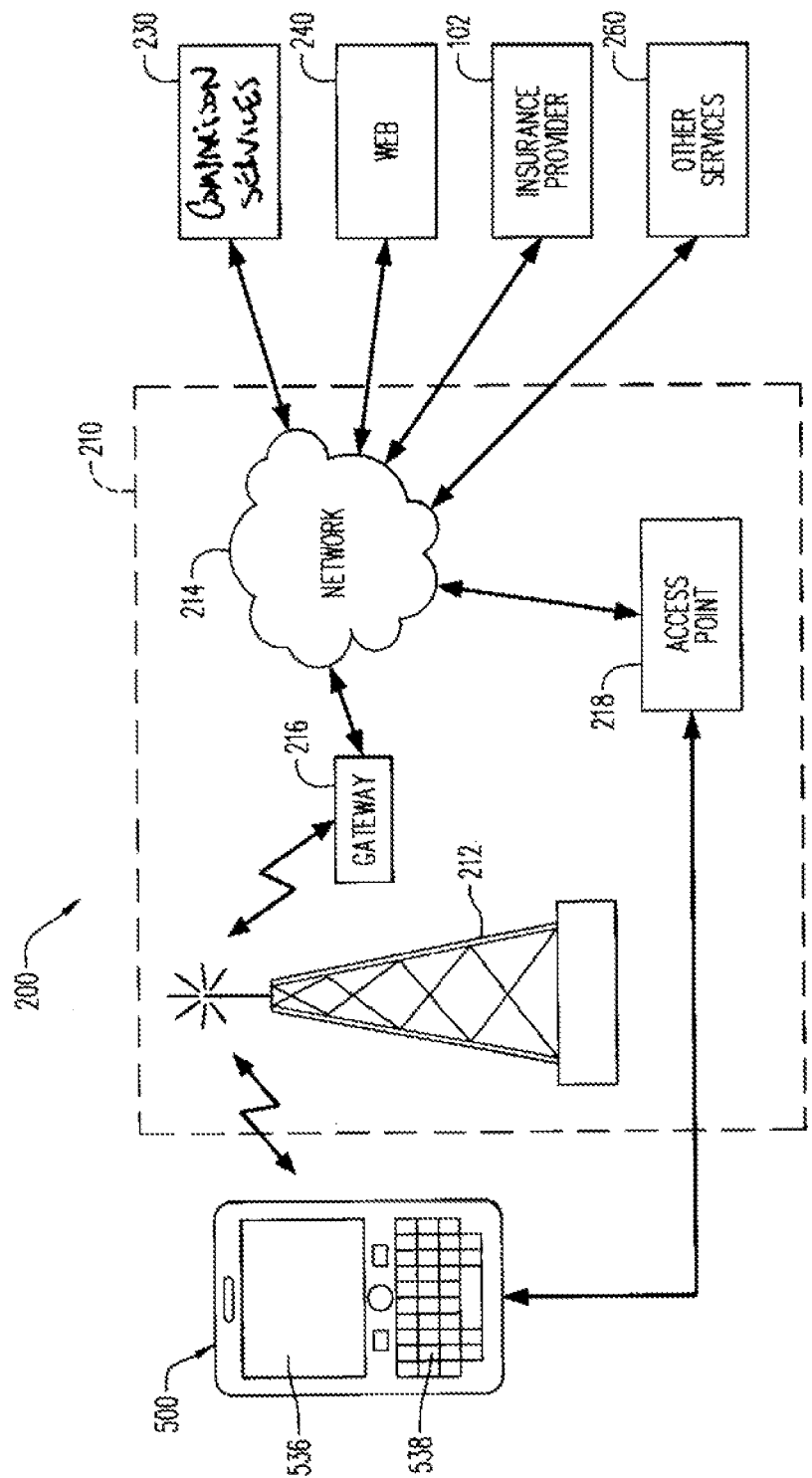
FIG. 2 illustrates a mobile system architecture within which some embodiments may be implemented.

Reference is now made to FIG. 2, which is a block diagram of an example network environment 200 showing communication paths between a mobile device 500 and the insurance provider systems 102 (as well as other devices and data sources). The mobile device 500 may be, for example, a mobile telephone, PDA, personal computer, or the like. For example, the mobile device 500 may be an iPhone® from Apple, Inc., a BlackBerry® from RIM, a mobile phone using the Google Android® operating system, a portable or tablet computer (such as the iPad® from Apple, Inc.), or the like. Pursuant to some embodiments, the mobile device 500 may be operated to capture data associated with one or more items of property, append meta data to the captured data (such as geocode data, time stamp data, user-input data such as tags, etc) and transmit the item data to an insurance provider 102 via a network 210. In general, mobile device 500 may be any mobile computing and/or communications device which is capable of executing the mobile insurance applications described herein.

The mobile device 500 of FIG. 2 can, for example, communicate over one or more wired and/or wireless networks 210. As an example, a wireless network can be a cellular network (represented by a cell transmitter 212). A mobile device 500 may communicate over a cellular or other wireless network and through a gateway 216 may then communicate with a network 214 (e.g., such as the Internet or other public or private network). An access point, such as access point 218 may be provided to facilitate data and other communication access to network 214. The access point 218 may be, for example, compliant with the 802.11g (or other) communication standards.

In some embodiments, mobile device 500 may engage in both voice and data communications over the wireless network 212 via access point 218. For example, the mobile device 500 may be able to place or receive phone calls, send and receive emails, send and receive short message service ("SMS") messages, send and receive email messages, access electronic documents, send and receive streaming media, or the like, over the wireless network through the access point 218. Similar communications may be made via the network 212.

In some embodiments, a mobile device 500 may also establish communication by other means, such as, for example, wired connections with networks, peer-to-peer communication with other devices (e.g., using Bluetooth networking or the like), etc.

The mobile device 500 can, for example, communicate with one or more services over the networks 210, such as service providers 230-260 and the insurance provider systems 102 (described above in conjunction with FIG. 1 and further below in conjunction with FIG. 3). For example, the mobile device 500 may communicate with one or more comparison services 230 to obtain comparative pricing information associated with an item scanned or entered using the mobile device 500. As another example, the mobile device 500 may communicate with one or more web services 240 to receive or transmit data to obtain product details, product warranty information, product replacement information or the like. As a specific example, in some embodiments, to provide further proof of ownership and/or price information The mobile device may also be in communication with a number of other service providers 260.

The mobile device 500 can also access other data over the one or more wired and/or wireless networks 210. For example, content providers, such as news sites, RSS feeds, web sites, blogs, social networking sites, developer networks, etc., can be accessed by the mobile device 500. Such access can be provided by invocation of a web browsing function or application (e.g., a browser) in response to a user launching a Web browser application installed on the mobile device 500.

The mobile device 500 can perform a number of different device functions which can be controlled or specified by the insurance company by providing instructions, data or commands to the mobile device 500. The instructions, data or commands may be executed by a processor of the mobile device 500 causing the mobile device 500 to be, effectively, under control of the insurance company allowing the insurance company to control the collection of inventory or property information from a user. The mobile device 500 may operate as a telephone, an email device, a network communication device, a media player device, etc., under control of one or more applications installed on the mobile device 500. In some embodiments, a user operating the mobile device 500 may interact with the applications using a keypad 538 which may be a tactile keypad with individual keys, or which may be a touch screen keypad. The user is presented with information and graphics on a display screen 536. For example, a user who is operating a mobile insurance application pursuant to the present invention may be presented with a series of user interfaces which may: (1) instruct the user how to capture data associated with an item of property, (2) how to categorize or label the item of property, (3) whether a serial number or unique identifier should be entered, and (4) what type of images to capture to properly identify the item. In some embodiments, upon submission of a new item of property to a user's inventory, one or more coverage rules may be invoked to determine if the addition of the item of property causes a policy limit or coverage to be exceeded. If so, further user interfaces may be presented to the user instructing the user on their options to remedy the deficiency (e.g., such as obtaining additional coverage, purchasing a special coverage rider, or the like). In some embodiments, information associated with obtaining any needed valuations, appraisals, or third party evaluations of property may also be provided (e.g., in the case of fine art, jewelry, or the like).

Figure 3:
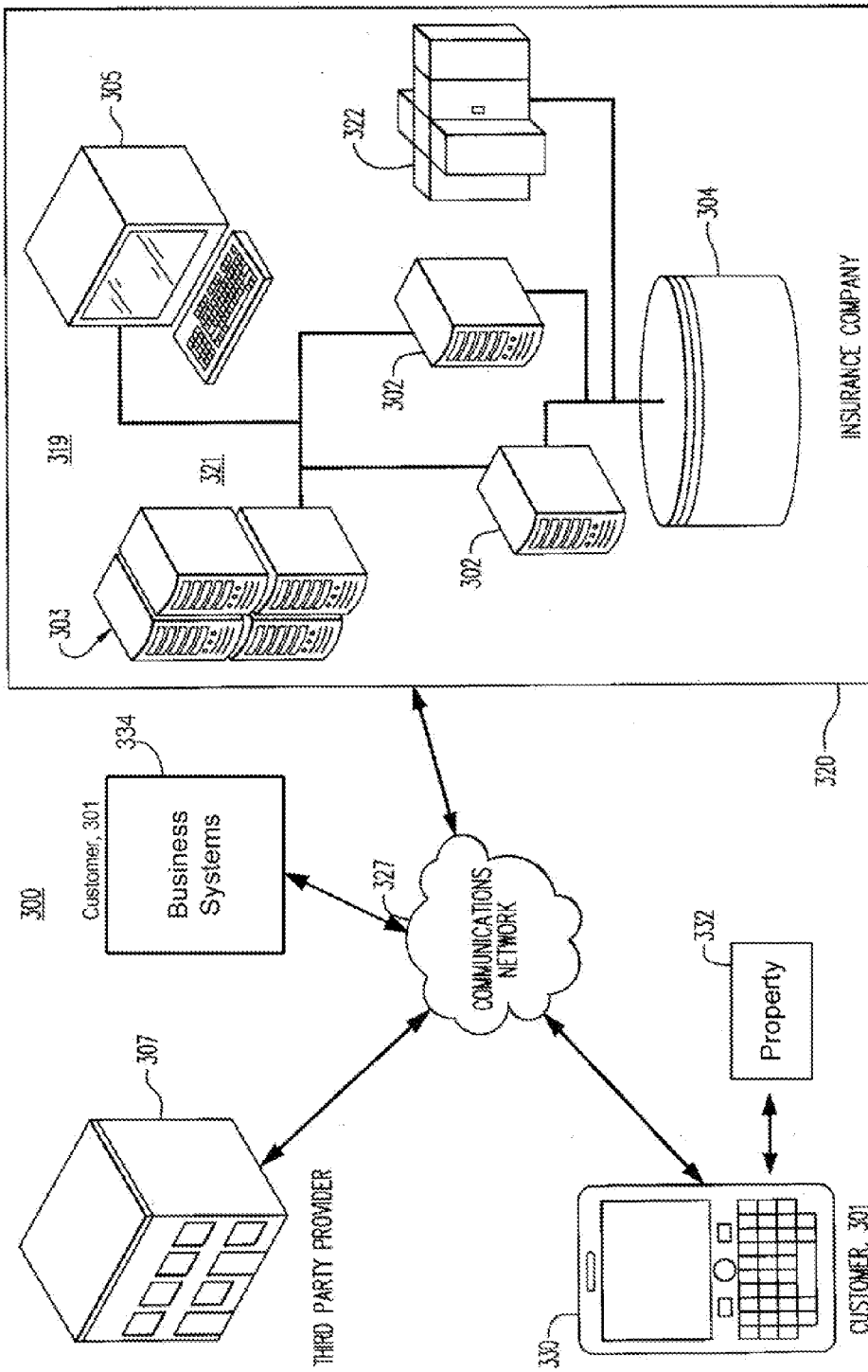
FIG. 3 is a block diagram of an insurance system pursuant to some embodiments.

Reference is now made to FIG. 3 which is a schematic diagram of a system 300 for collecting property data, evaluating and providing feedback on insurance, such as insurance related to, or whose pricing is dependent at least in part on items of property including personal property. In FIG. 3, insurance company 320 provides a number of different customers (each labeled as customer 301) with insurance coverage. The type of insurance provided by insurance company 320 may be any type of insurance under which claims of property loss may be incurred, although the present invention is described primarily in terms of personal property insurance (such as homeowner's or renter's policies) and commercial lines insurance (such as insurance for a retailer or business that carries or holds inventory or equipment). Insurance company 320 can simultaneously provide services to multiple customers, including multiple different types of customers.

Customers 301 may choose to interact with insurance company 320 using features of the present invention using different input or data capture devices. For example, in some embodiments, to be discussed further herein, customers such as customer 301 may operate a mobile device 330 configured to operate using a mobile insurance application pursuant to the present invention in order to capture, transmit, and update information about one or more items of property owned by the customer. As another example, in some embodiments, customers such as customer 301 may operate business systems 334 to capture, transmit and update information about items of property. For example, business systems 334 may include point of sale systems (in the case of a customer that is a retailer), inventory systems (for retailers, warehouses, wholesalers, or the like), or other computer systems (such as personal computers or the like). Embodiments of the present invention allow for such customers to easily capture, transmit and update information about items of property to insurance company 320 for use in establishing an insurance inventory as well as for use in ensuring that the items of property are adequately covered by insurance policies.

Mobile device 330, pursuant to some embodiments, stores a mobile insurance application program that may be loaded onto the mobile device 330 from an insurance company 320 or from an application repository (e.g., such as Apple's App Store or the like). The application, when launched, prompts the customer 301 for information used to interact with the insurance company 320 or to collect and provide property information to the insurance company 320. A variety of different types of data and information may be provided from mobile device 330 to insurance company 320, including static data regarding the customer 301, such as the customer's name, address, contact information, policy information, etc. Other variable information may be provided (as described in each of the mobile application embodiments described herein). Dynamic or collected data may also be provided by collecting data from one or more sensor(s) 332 in communication with the mobile device 330.

Insurance company 320 has a computer system 319 that includes application servers 302, load balancing proxy servers 303, data storage unit 304, business logic computer 322, and user interface module 305 to perform risk evaluation and underwriting based on the collected property data and policy information. Employees of the insurance company 320 and other authorized personnel use user interface module 305 to access the insurance company computer system. User interface module 305 may be any type of computing device that is configured to communicate with other computer systems. User interface module 305 may be connected directly to application server 302, or may access an application server 302 via the load balancing proxy servers 303. User interface module 305 may connect to load balancing proxy servers 303 via a local area network, a private data link, or via the internet.

Although depicted as being part of insurance company 320 in FIG. 3, user interface module 305 may be located remotely. The business logic computer 322 is connected to the data storage unit 304 and application servers 302 over a local area network 321, which may be part of communication system 327. In addition, other network infrastructure, including, for example a firewall, backup servers, and back up data stores, may also be included in the system 319, without departing from the scope of the invention. Communications over the local area network 321 and/or over the Internet, in one implementation, may be encrypted. In addition, such communications, whether encrypted or not, may also be digitally signed for authenticating the source of the communications. The computer system 319 may also include a certificate authority to authenticate one or more of the communications using public key infrastructure.

Based on property data collected from the mobile device 330 and any third party data sources, an evaluation module analyzes and evaluates data associated with a customer 301. As used herein, a "module" may be implemented in software for execution by various types of processors. An identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

As used herein, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. In addition, entire modules, or portions thereof, may also be implemented in programmable hardware devices such as field programmable gate arrays, programmable array logic, programmable logic devices or the like or as hardwired integrated circuits.

A number of different business logic modules may be operated by insurance company 320 to process data collected by mobile devices 330. For example, an underwriting module may be implemented, for example, in business logic computer 322, and used to underwrite or alter insurance pricing, coverage limits or policy exclusions for customer 301 based on the received property and inventory data. The business logic module may use predictive models, such as neural networks, Bayesian networks, and support vector machines, in performing the underwriting and premium or coverage adjustment. In one embodiment, the business logic module operates as a coverage engine to analyze the current policy coverage associated with an individual based on the value of the individual's reported inventory of property. For example, in the event that the total reported replacement value exceeds the coverage limits, the coverage engine may notify the customer so that an appropriate policy adjustment may be made. As another example, in the event that the total reported replacement value is less than the coverage limits, the coverage engine may notify the customer that they are over insured and may suggest policy adjustments accordingly. As a still further example, in the event that an item or items to be added are excluded from coverage, the coverage engine may notify the customer that the item(s) are excluded and may propose policy adjustments (such as a rider to provide the additional coverage).

In some embodiments, insurance company 320 may award a customer 301 that uses the system of the present invention to maintain their property inventory by providing premium discounts, or other advantageous rewards, simply for agreeing to use (and, in some embodiments, actually using) the mobile applications as described above. Insurance company 320 may award different discounts depending on the nature and amount of data provided by customer.

In one implementation, software operating on the application servers 302 act merely as presentation and data extraction and conversion servers. All substantive business logic, including underwriting and pricing determinations, is carried out on the business logic computer 322. In this implementation, the application servers 302 obtain data from the data storage unit 304 and the business logic computer 322 and incorporate that data into web pages (or other graphical user interface formats). These web pages are then communicated by the application servers 302 through the load balancing proxy servers 303 to user interface module 305 for presentation. Upon receiving input from user interface module 305, the application server 302 translates the input into a form suitable for processing by the business logic computer 322 and for storage by the data storage unit 304. In this implementation, the application servers can be operated by third parties, who can add their own branding to the web pages or add other customized presentation data. Alternatively or in addition, at least some of the business logic is also carried out by the application servers 302.

In some embodiments, the application servers 302 are software modules operating on one or more computers. One of the computers on which the application servers 302 are operating may also serve as the business logic computer 322 and/or as a load balancing proxy server 303.

In some embodiments, the software operating on user interface module 305 includes a thin or thick client application in addition to, or instead of a web browser. The thin or thick client application interfaces with a corresponding server application operating on the application server 302.

Figure 4:
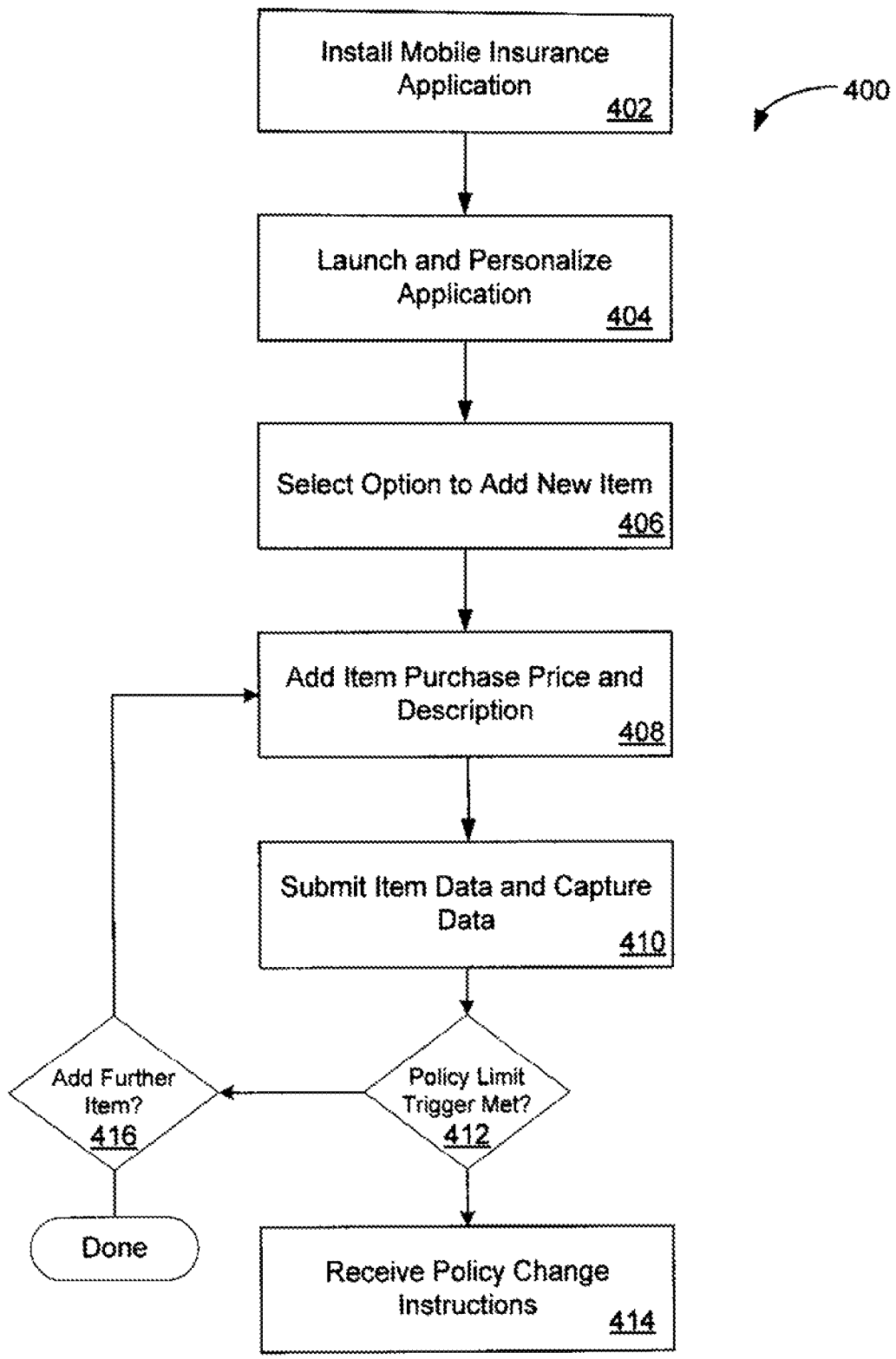
FIG. 4 is a flow diagram depicting a proof of ownership process pursuant to some embodiments.

Reference is now made to FIG. 4 which is a flow diagram depicting a process 400 for installing and operating a mobile insurance application pursuant to some embodiments. Some or all of the steps of process 400 may be performed using a mobile device such as the mobile device 104 of FIG. 1 (or the mobile device 500 described in further detail below in conjunction with FIGS. 5 and 6). As shown, processing begins at 402 where a user operating a mobile device 500 installs a mobile insurance application. The mobile insurance application may be installed from the mobile device (e.g., by interacting with an application download system), or from a personal computer in communication with the mobile device. The application may be downloaded from the insurance company 320 or from an application marketplace (such as the iTunes® Store or Android® Store).

The user then launches the mobile application at 404 and enters information to personalize the application. For example, the user may be prompted to enter information about themselves as well as their policy information so that the mobile insurance application may communicate with the insurance company and so that the user's policy information may be monitored and updated based on the property information entered by the user after the application has been personalized. In some embodiments, the user may be prompted to enter verification information used to authenticate the user with the insurance systems.

Processing continues at 406 where the user, operating the mobile insurance application, selects an option to add a new item of property to the user's property inventory. At 408 the user interacts with a user interface or series of user interfaces of the mobile insurance application to enter information about an item to be added to their inventory, including entering information such as the item purchase price and description. The mobile application may also prompt the user to capture specific information about the item, such as one or more photographs of the item, a serial number, it's location within a residence or insured property of the user, etc. At 410, the item data obtained at 408 and other data captured by the mobile device (such as a time stamp, geocode information, and the like) are submitted to an insurance company over a wireless network. The insurance company receives the information, uses it to update an inventory database (such as the database shown below in FIG. 9) and analyzes the updated inventory and item information to determine (at 412) if the information triggers any policy limits or other rules.

A policy limit or other rule may be triggered in any of a number of different ways, depending on the rules of the insurer. For example, a policy limit may be triggered if the addition of the item at 408 causes the total property value of the user to greatly exceed any policy limits. In such a situation, processing may continue at 414 where instructions or information about the issue are presented to the user on the mobile device. For example, at 414 a notification may be presented to the user that they are under-insured for their personal property, and may suggest that a policy rider be obtained or some other increase to the policy limits. In some embodiments, the user may apply for (and in some situations, bind) the additional coverage by interacting with the mobile insurance application on their mobile device.

Policy limit triggers may also be met if the user is underinsured, in which case processing at 414 may include notifying the user that they are over-insured. Instructions on reducing their coverage may be provided and executed using the mobile insurance application.

In the event that the addition of the item does not meet or set a policy limit trigger, processing continues at 416 where a determination is made whether the user has additional items of property to add to their inventory. If yes, processing repeats at 408 and the further items are added. If no, processing terminates. The user may launch and interact with the mobile insurance application as needed to add further items of property to their inventory. In this manner, embodiments allow users to maintain an accurate and up to date inventory of insured property, while receiving immediate recommendations and notifications if the addition requires changes to their existing policy.

Further details of some embodiments of mobile devices that may be used in conjunction with embodiments of the present invention will now be described by reference to FIGS. 5 and 6. Reference is first made to FIG. 5, where details of a mobile device 500 according to some embodiments is shown. As depicted, the mobile device 500 includes a number of components which may be controlled or perform functions in conjunction with one more application programs 510-512 to perform the features of some embodiments.

The mobile device 500 can include a memory interface 502 one or more data processors, image processors and/or central processing units 504, and a peripherals interface 506. The memory interface 502, the one or more processors 504 and/or the peripherals interface 506 can be separate components or can be integrated in one or more integrated circuits. The various components in the mobile device 500 can be coupled by one or more communication buses or signal lines.

Sensors, devices and subsystems can be coupled to the peripherals interface 506 to facilitate multiple functionalities. For example, one or more sensors, including biometrics sensors 514 and 528, an accelerometer 516, a photoelectric device 516, a proximity sensor 520, a camera 522, a wireless communication unit 524, and an audio unit 526 may be provided to facilitate the collection, use and interaction with data and information and to achieve the functions of the insurance applications described herein.

The mobile device 500 may include one or more input/output (I/O) devices and/or sensor devices. For example, input controllers 534 may be provided with a speaker and a microphone (not shown) to facilitate voice-enabled functionalities, such as phone and voice mail functions. In some implementations, a loud speaker can be included to facilitate hands-free voice functionalities, such as speaker phone functions. An audio jack can also be included for use of headphones and/or a microphone.

The I/O subsystem 530 can include a touch screen controller 532 and/or other input controller(s) 534. The touch-screen controller 532 can be coupled to a touch screen 536. The touch screen 536 and touch screen controller 532 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch screen 536.

The other input controller(s) 534 can be coupled to other input/control devices 538, such as one or more buttons, rocker switches, thumb-wheel, infrared port, USB port, and/or a pointer device such as a stylus. The one or more buttons (not shown) can include an up/down button for volume control of the speaker and/or the microphone. In some implementations, a proximity sensor 520 can be included to facilitate the detection of the user positioning the mobile device 500 proximate to the user's ear and, in response, to disengage the touch-screen display 536 to prevent accidental function invocations. In some implementations, the touch-screen display 536 can be turned off to conserve additional power when the mobile device 500 is proximate to the user's ear.

Other sensors can also be used. For example, in some implementations, a photoelectric device 518 may be provided to facilitate adjusting the brightness of the touch-screen display 538. In some implementations, an accelerometer 516 can be utilized to detect movement of the mobile device 500. In some embodiments, the mobile device 500 may include circuitry and sensors for supporting a location determining capability, such as that provided by the global positioning system (GPS) or other positioning system (e.g., systems using Wi-Fi access points, television signals, cellular grids, Uniform Resource Locators (URLs)). In some implementations, a positioning system (e.g., a GPS receiver) can be integrated into the mobile device 500 or provided as a separate device that can be coupled to the mobile device 500 through a peripherals interface 506 to provide access to location-based services.

The positioning and location-based services may be used, for example, to tag data transmitted from the mobile device 500 to insurance provider systems 102. For example, such location data may be appended to product information captured by a mobile device using a mobile insurance application. The geo location data may assist the insurance company in verifying that an insured actually purchased an item for their own use and may also be used to verify that a claimed item of personal property was located at the location claimed by an insured. For example, an insured who carries a homeowner's policy and who uses features of the present invention to create an inventory of personal property may take pictures of each item of property. Each of the pictures may be geotagged with location information provided by the positioning and location-based services of the mobile device 500. If the homeowner makes a claim under the policy alleging that one or more of the inventoried items was damaged or otherwise impaired, the processing of the claim may verify that the items were located (at least when inventoried) at the insured's home. In this way, location based data may be used to enhance claims processing, thereby reducing fraudulent claims and improving the insurer's ability to quickly and accurately process claims.

The mobile device 500 can also include a camera lens and sensor 520. In some implementations, the camera lens and sensor 520 can be located on the back surface of the mobile device 500. The camera can capture still images and/or video. The camera may be used, for example, to capture images of items of personal (or real) property to be added to an insured's inventory. In some embodiments, the camera can also be used to capture and process bar codes, serial numbers, product codes and other identifying information associated with each item being inventoried. Such identifying information may be stored in or accessible to an inventory system (such as the system 108 of FIG. 1) and used to obtain pricing associated with items that have been inventoried (e.g. such as current market valuations or replacement costs of products that have been inventoried).

The mobile device 500 can also include other sensors, including, for example, sensors used to verify the authenticity or quality of an item of property to be added to a user's inventory. For example, a mobile device 500 may be coupled to (or configured with) a sensor designed to determine the quality of an object, such as a diamond, precious metal, or the like. The mobile device 500, using the sensor, may perform an analysis and append the resulting data to a record transmitted to an insurance company or other entity for further use or analysis. The mobile device 500, using the sensor, may also capture qualitative data about an object and transmit the data to an insurance company or one or more third parties for analysis. The data may also be stored in the user's product inventory for use in analyzing a loss claim in the future (e.g., to determine whether and how much of a claim should be paid).

The mobile device 500 can also include one or more wireless communication subsystems 524, such as an 802.11b/g communication device, and/or a Bluetooth® communication device. Other communication protocols can also be supported, including other 802.x communication protocols (e.g., WiMax, Wi-Fi), code division multiple access (CDMA), global system for mobile communications (GSM), Enhanced Data GSM Environment (EDGE), 3G (e.g., EV-DO, UMTS, HSDPA), etc.

In some implementations, additional sensors or subsystems may be coupled to the peripherals interface 506 via connectors such as, for example a Universal Serial Bus (USB) port, or a docking port, or some other wired port connection.

The memory interface 502 can be coupled to memory 508. The memory 508 can include high-speed random access memory and/or non-volatile memory, such as one or more magnetic disk storage devices, one or more optical storage devices, and/or flash memory (e.g., NAND, NOR). The memory 508 can store an operating system, such as Darwin, RTXC, LINUX, UNIX, OS X, WINDOWS, or an embedded operating system such as VxWorks. The operating system may include instructions for handling basic system services and for performing hardware dependent tasks. In some implementations, the operating system can be a kernel (e.g., UNIX kernel).

The memory 508 may also store application programs 510-512 which act, in conjunction with the processors 504, to cause the mobile device to operate to perform certain functions, including the insurance processing and product inventory related functions described herein.

The memory 508 can also store data, including but not limited to documents, images, video files, audio files, and other data. In some implementations, the memory 508 stores address book data, which can include contact information (e.g., address, phone number, etc.) for one or more persons, organizations, services, or entities. For example, in some embodiments, the memory stores insurance policy numbers or other unique identifiers to allow a user of the mobile device 500 to quickly access insurance policy related data and information. In some embodiments, product or item data collected under control of the mobile insurance application may be stored in the memory 508 (either temporarily or for longer periods).

Figure 6:
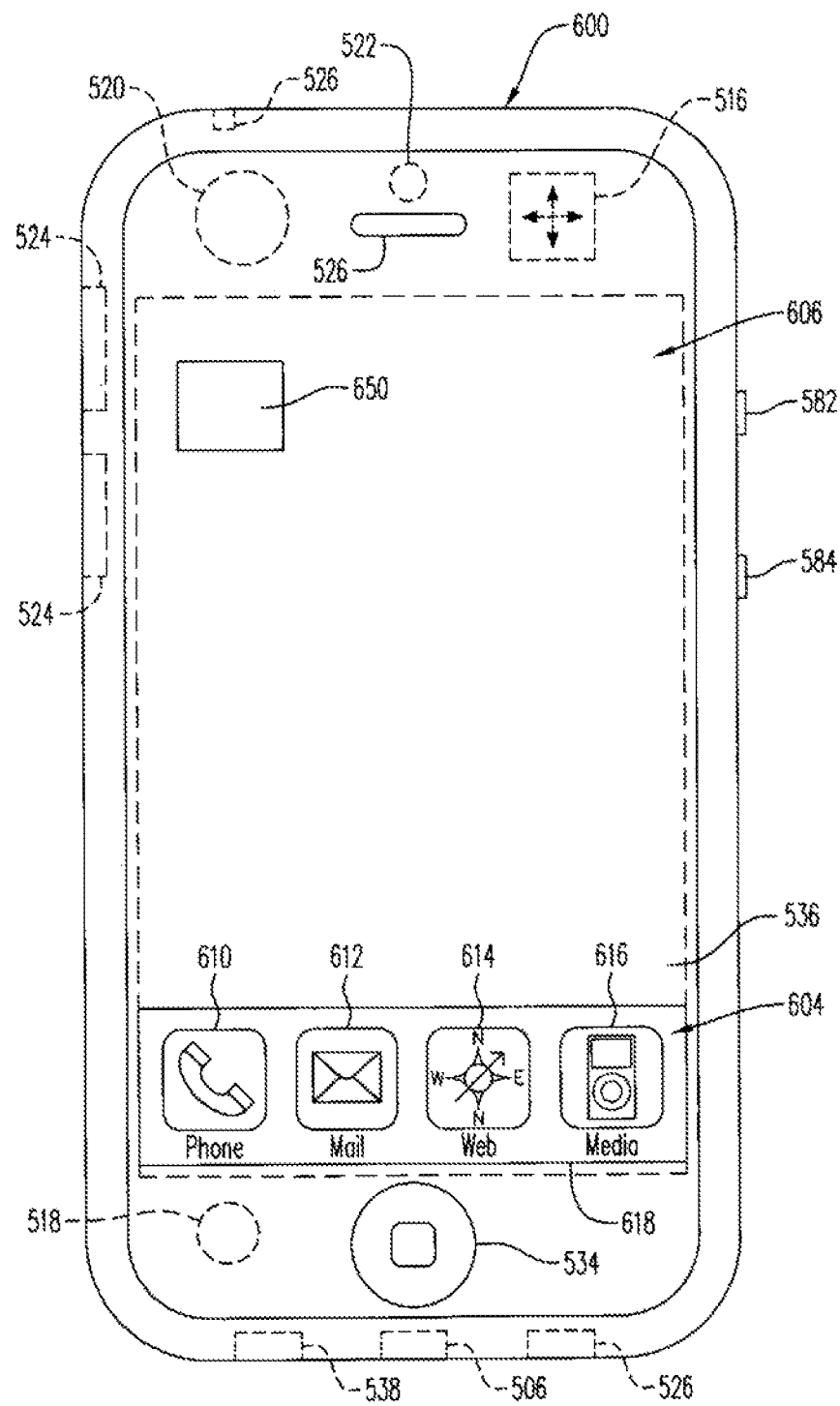
FIG. 6 is a block diagram of the mobile device of FIG. 5.

Reference is now made to FIG. 6, where a mobile device 500 is shown. As shown, the mobile device 500 can launch (and operate under the control of) one or more application programs by selecting an icon associated with an application program. As depicted, the mobile device 500 has several application programs (and corresponding icons), including an mobile insurance application (launched by selecting icon 650), a phone application (launched by selecting icon 610), an email program (launched by selecting icon 612), a Web browser application (launched by selecting icon 614), and a media player application (launched by selecting icon 604). Those skilled in the art will recognize that mobile device 500 may have a number of different icons and applications, and that applications may be launched in other manners as well (e.g., using hot keys, drop down selectors, or the like). For example, a user may have more than one mobile insurance application installed (e.g., such as one mobile insurance application configured to capture, store and provide information about the user's inventory of items covered by a homeowner's insurance policy, and a second mobile insurance application configured to capture, store and provide information about the user's inventory of items covered by a commercial lines insurance policy). In the embodiment shown, an application, such as the mobile insurance application, is launched by the user tapping or touching an icon displayed on the touch screen 536 interface of the mobile device 500.

Once an application is launched, the user may interact with the application, and the mobile device may function pursuant to the program instructions associated with the application. In the mobile insurance applications described herein, details of some aspects of the operation of the mobile device 500 are described; however, those skilled in the art will appreciate that a number of different functions and operational features may be provided.

Figure 7:
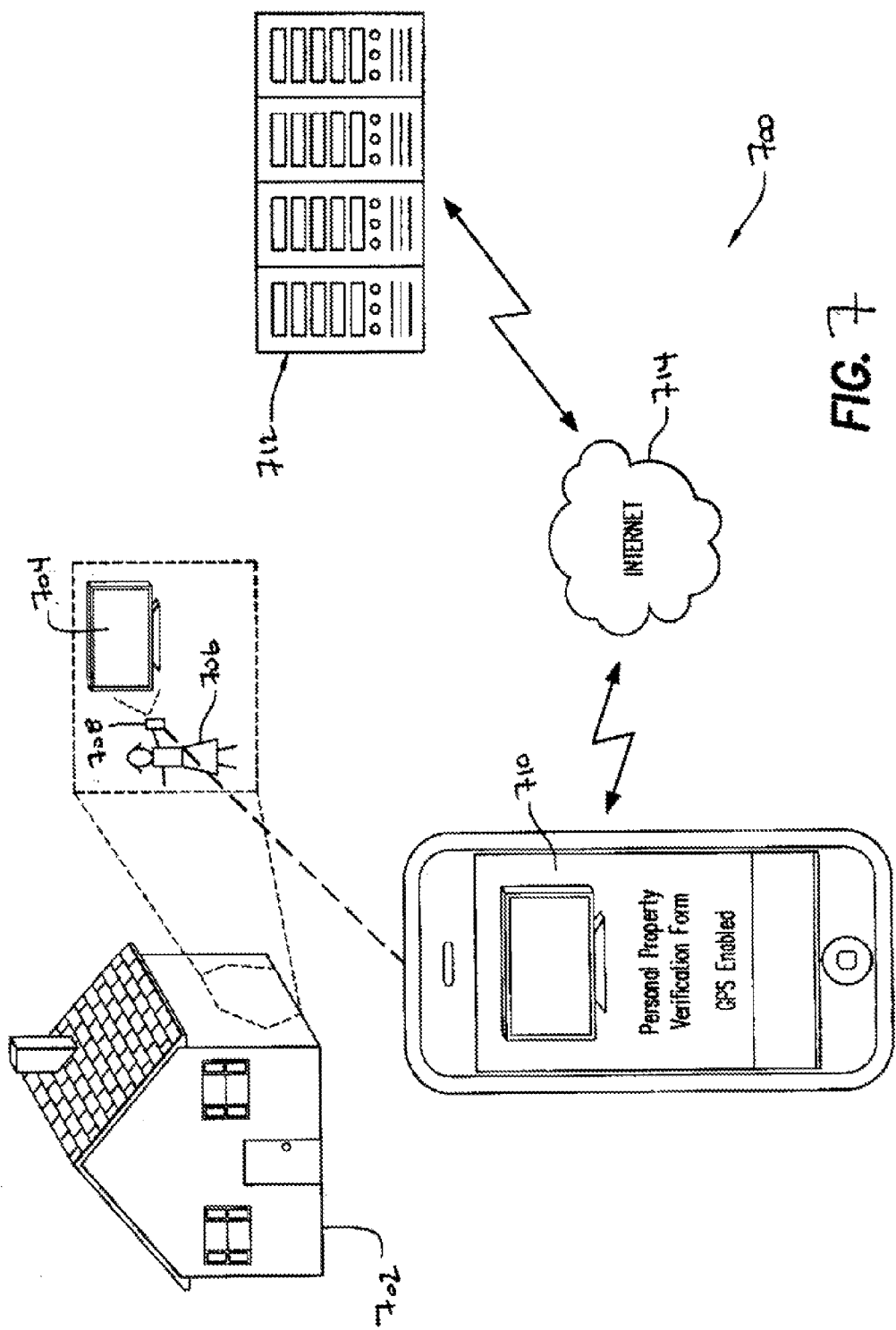
FIG. 7 is a block diagram depicting a proof of ownership system pursuant to some embodiments.

Reference is now made to FIG. 7, which shows a block diagram 700 of a mobile device 708 being used to capture and transmit data associated with an item of property using a mobile insurance application pursuant to the present invention. The block diagram 700 depicts a homeowner using features of the present invention to add an item of property to her insurance inventory. However, similar features and processes may be used in conjunction with commercial or other types of insurance and users. As shown, a homeowner 706 is shown operating a mobile device 708 to capture data associated with a television 704 that is located in the homeowner's home 702. For example, the homeowner 706 may be using features of the present invention to create an inventory of existing items in her home or she may be adding a newly purchased television 704 to an existing inventory.

In either event, the homeowner 706 captures information identifying the television 704 using a mobile device 708. As shown, the mobile device 708 captures an image or digital photo of the television 704. The captured image may be displayed to the homeowner 706 so the homeowner can confirm that the image was properly captured and so the homeowner can add other information associated with the item. For example, a personal property verification form 710 may be displayed on a display device of the mobile device 708 prompting the user to enter further data associated with the item. A number of different items of data may be provided by the user including, for example: a product model number, a serial number, a purchase price, a purchase date, warranty information, the purchase location, or the like. Some or all of the data may be captured as images or scanned using the mobile device 708 and appended to an inventory record in the mobile device 708 for transmission to an insurance system 712. In addition to data entered or captured under control of the user, additional meta data may be captured and appended to the inventory record. For example, in some embodiments, each record includes a time stamp showing when the image or data was captured. In some embodiments, each record may include location data such as geocode information identifying where the image or data was captured. This data is transmitted to the insurance system 712 under control of a mobile insurance application executed on the mobile device 708. Each record transmitted to the insurance system 712 may further appended with data identifying the user and the user's insurance provider or policy information. In some embodiments, the records transmitted from the mobile device 708 are stored in, or accessible to, an inventory system database allowing access, retrieval, updating and further interaction by the user.

In some embodiments, when a new item of personal property (such as the television 704) is added to an insured individual's inventory, the insurance system 712 invokes a coverage engine or process to analyze whether the addition of the item causes the insured's inventory of property to exceed the limits of coverage under the applicable insurance policy. For example, if the homeowner 706 has a policy with $100,000 of coverage for personal property, and the addition of the new television 704 causes the value of the homeowner's inventory to exceed $100,000, a process may be triggered to notify the homeowner of the fact that she may be underinsured. In some embodiments, the mobile insurance application, operating in conjunction with the insurance systems 712, may provide the insured with an option to purchase additional coverage to ensure that the insured's property is appropriately covered. The data collected using such techniques may be used by insurance providers and other entities to make insurance related decisions where legally allowed.

Similar techniques may be used to capture information about a number of different items of property at once. For example, the mobile device 708 may be operated to capture video images of a room in the house 702. All of the items in the room may be identified using image processing and each added to the user's insurance inventory maintained at the insurance systems 712. The homeowner may tag or add additional information (including information about the date acquired, notes about value, etc) by interacting with the insurance systems 712 using the mobile device 708 or other computing devices. A copy of the video images may be stored in conjunction with the inventory to assist in proving ownership of the items in the inventory. The video images may further be geotagged with location information to provide further evidence of the location of the items (e.g., to show that the items were, indeed, in the user's home or place of residence).

In some embodiments, the user may be prompted or reminded to perform updates to the inventory on a regular basis. For example, a user may be prompted to perform a full inventory of her home or residence on an annual basis in order to qualify for insurance benefits (or, simply to ensure that the insurance inventory is up to date and to confirm that the user is properly insured for her items of property).

Similar techniques may be used to capture information about items of commercial property, such as items of inventory or equipment. As an example, the building 702 may be a retail store and a mobile device 708 may be operated by an employee 706 to capture information about items of inventory in stock. Individual images may be captured of each item or video images may be captured to identify multiple items of property. In some embodiments, the mobile device 708 may further be in communication with an inventory system of the retailer, allowing information about each item in stock to be easily added to the insurance inventory associated with the retailer. In this manner, retailers and other commercial entities may easily add items to their insurance inventory and receive a determination of whether sufficient coverage for the items of property exist.

Reference is now made to FIGS. 8 and 9 which show portions of data tables that may be stored at, or accessible to, an insurance company such as, for example, the insurance company 320 of FIG. 3. FIG. 8 represents a portion of an insurance policy database 800, and FIG. 9 represents a portion of an inventory database 900. Those skilled in the art will appreciate that other data fields and tables will likely be used to fully define and describe policy databases and inventory databases and that the portions of tables shown are for illustrative and explanatory purposes only. FIG. 8 is a tabular view of a portion of a policy data table 800 in accordance with some embodiments of the present invention. The table 800 includes a number of entries identifying different insurance policies involving personal property (or other types of property) for which an inventory or identification of specific items of property may be provided pursuant to the present invention. The data in policy table may be created, for example, when new policies are issued by insurance systems such as the insurance system 300 of FIG. 3.

The table 800 defines a number of fields including, for example, a policy number 802, a policy type 804, policy limits 806, a current property value 808, deductibles 810 and information whether an alarm system have been installed 812. The policy number 802 may be a system generated identifier that is used to uniquely identify different policies issued by and/or administered by the insurance company 320. The policy type 804 may be an indicator that identifies the type of policy (e.g., such as a personal policy, a homeowner's policy, a commercial lines policy, or the like). The type of policy may be used to select different rules and procedures relating to the assessment of insurance coverage. Limits 806 may include information identifying any coverage limits associated with the policy identified by policy identifier 802. The coverage limits 806 may be used in an analysis of whether an existing coverage is sufficient to cover the policy holder given the policy holder's current inventory of property. The coverage limits 806 may also include exclusions identifying any types of items of property that are excluded from coverage by the policy identified by policy identifier 802.

Current property value 808 is a value (or values) that represent the total current value of property associated with a policy based on information provided by the policy holder using the system of the present invention (including, for example, the total value of all items in the policy holder's inventory such as shown below in FIG. 9). The current property value 808 may be updated each time the policy holder updates, adds, or removes items of property from their inventory. In some embodiments, if the current property value 808 exceeds the limits 806 for a policy, the policy holder may be notified of the potential that their property is underinsured (and may wish to increase their coverage). In some embodiments, if the current property value 808 is below the limits 806, the policy holder may be notified of the potential that they are over insured (and may wish to reduce their coverage).

Deductible 810 includes information identifying any deductibles associated with the policy identified by policy identifier 802. In some embodiments, if certain participation conditions are met (such as maintaining an up-to-date inventory, keeping the current property value 808 below the limits 806, and securing the property using an alarm system), the deductibles may be reduced or modified.

Alarm field 812 includes information identifying whether the property insured by the policy identified by policy identifier 802 is secured by an approved alarm system. In some embodiments, policy holders who have an approved home, residence or business alarm system may qualify for improved benefits (such as reduced deductibles or increased coverages or limits).

Those skilled in the art will appreciate that other types of data may also be provided to identify individual policies; the fields shown in FIG. 8 are for illustrative purposes only. Further, embodiments may be used with other types of policies and coverages with desirable results.

Reference is now made to FIG. 9 where a portion of an inventory data table 900 is shown. Inventory data table 900 may be stored at, or accessible to, the insurance company 320 of FIG. 3 and may be used in conjunction with mobile devices 330 and other interfaces (such as Web browsers) by insured individuals to track, monitor and report their inventory of items that are to be covered by an insurance policy issued by the insurance company 320. Those skilled in the art will appreciate that other data fields and tables will likely be used to fully define and describe policy databases and inventory databases and that the portions of tables shown are for illustrative and explanatory purposes only. FIG. 9 is a tabular view of a portion of an inventory data table 900 in accordance with some embodiments of the present invention. The table 900 includes a number of entries identifying specific items of property associated with an insurance policy. The data in inventory table may be created, for example, when policy holders add or update their inventory using a mobile device 330. Data in inventory table 900 may be deleted or removed (or marked as no longer in the policy holder's inventory) when the policy holder indicates that the property has been sold or otherwise disposed of. For example, in some embodiments relating to commercial lines policies, items may be removed from the table 900 when an item is sold. Information about such sales may be retrieved or provided from point of sale or other merchant systems, allowing table 900 to automatically reflect the current status of a retailer's inventory.

The table 900 defines a number of fields including, for example, a customer identifier 902, a policy number 904, an item descriptor 906, a serial number 908, photo(s) 910, capture data 912, a date acquired 914, a purchase price 916, a replacement price 918 and an estimated value 920. Each customer (identified by a unique customer identifier 902) may have a number of items of property in the inventory table, and may also have one or more policy numbers 904 for which items of property are provided. Each item of property in a customer's inventory may include a descriptor 906 which may include a description provided by the customer or a descriptor captured by scanning an image, bar code, UPC or other information from the product. Some items may have serial numbers 908 or other unique identifiers, which may be used to identify warranty information or otherwise prove ownership of an item in the event a claim is made resulting from a property loss.

One or more photos or other images 910 of the item may be provided (e.g., such as those captured by a camera associated with a mobile device when adding the item to the inventory). One or more items of capture data 912 may also be provided. Capture data 912 may include geocode data, time stamp data, or other captured by the mobile device when the item was added to the inventory database. A date acquired 914 and purchase price 916 may also be entered. Pursuant to some embodiments, a replacement price 918 and estimated value 920 may be provided which are based on data retrieved from external sources. For example, in the case of a replacement price for a television, the value shown in field 918 may be obtained on a periodic basis by retrieving comparable price information from liquid markets for the product. In the case of a television, for example, comparable price information for the make, model and year of the television may be obtained from eBay or other aftermarkets. The data may be retrieved by scraping or in other automated fashion to automatically update data in replacement price field 916 as needed. Similarly, an estimated value 920 may be obtained by retrieving data from publicly available feeds or sources of pricing information for a comparable product.

The data from the inventory database 900 may be updated on a regular basis. Some of the data is updated by customers as they add, update or remove items from their inventory. Other items of data may be programmatically updated on a regular or other basis by retrieving data from third party sources. For example, in some embodiments, data may be retrieved from credit card or banking systems to update information about items of property. As an example, a user may allow the inventory database 900 to access an electronic banking system and update the inventory database 900 with information about items purchased by the user each month. The user may then manually edit information about each item to provide further details or to specify that an item was purchased as a gift for another or otherwise is not intended to be included in the user's insurance coverage analysis. Such an interface may allow the inventory database 900 to receive product information as well as a purchase price and purchase date.

As a further example, inventory database 900 may be configured to receive information from merchant inventory or point of sale systems, allowing the database 900 to automatically update as inventory is received and as inventory is disposed of In this manner, a retailer may create an insurance inventory that accurately matches their actual inventory, allowing the insurance company to offer accurate pricing and coverage for the retailer's actual inventory.

The combination of data may be used to trigger coverage analyses of each policy, generating automated notifications to policy holders and agents of situations where action may be required (e.g., such as in the case where a customer is under or over-insured based on the information in their inventory). Further, in the event that a customer makes a claim associated with a covered loss, the data from inventory database 900 may be used to quickly, efficiently, and accurately resolve and settle the claim.

Thus, embodiments of the present invention may improve the information available to insurers to allow them to better underwrite and administer insurance policies that are based on or related to an insured's property. Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

For example, while features have been described where the policy holder operates a mobile device to capture property information, in some embodiments, agents or third parties may capture property information on behalf of the policy holder or on behalf of an insurance company. As an illustrative example, a moving company may use one or more mobile devices configured pursuant to the present invention to create an inventory of a customer's property prior to a move. For example, employees of the moving company may capture information about each item of property as the items of property are boxed or otherwise prepared for shipping. A label, sticker (such as a bar coded tag) or electronic tag (such as an RFID tag) may be affixed to each item and scanned to uniquely identify each item as it is inventoried. Once all of the items have been placed into the inventory system, a price or coverage quotation may be issued by an insurance company to insure the customer during the moving process. A further quotation may also be provided to insure the property at the customer's destination (e.g., to issue a new homeowner's policy or renter's policy). Those skilled in the art will recognize that other features or modifications may also be provided.

What is claimed is:
1. A computer system, comprising:
   a mobile device, coupled to a sensor for determining quality of items, and configured to execute an application program to capture an image of a first item, generate an interface prompting a user for data relating to the first item, activate the sensor to determine quality of the first item, perform an analysis based on data from the sensor, prompt the user to capture, via a camera of the mobile device, an image of one or more of a bar code, serial number or product code of the first item, receive in response to the prompt an image of one or more of a bar code, serial number or product code of the first item, communicate with one or more comparison services to obtain comparative pricing information associated with the first item employing the at least one of bar code, serial number or product code, and automatically transmit a record including the captured image data, data entered via the user interface, location information automatically captured via a GPS receiver of the mobile device, time information, the image of one or more of a bar code, serial number or product code of the first item, the obtained comparative pricing information, quality data received from the sensor and data resulting from the analysis; the application program being further configured to, responsive to receipt of a response to a request to add an item, automatically display the received response on an interface of the mobile device;
   a data storage device storing, updating and providing access to data defining a plurality of insurance coverage;
   a computer processor for executing program instructions and for retrieving said data defining a plurality of insurance coverage rules from the data storage device;
   a memory, coupled to the computer processor, storing program instructions for execution by the computer processor to:
      receive, from the mobile device, the transmitted record;
      analyze stored property inventory data including said received record information, including said comparative pricing information, to determine a current total value of a property inventory including a value of said at least first item to be added;
      compare said property inventory, said current total value of said property inventory, said location information and said information identifying said at least first item to be added with said data defining a plurality of insurance coverage rules, said plurality of insurance coverage rules including at least a first geographical limit; and
      generate and transmit to the mobile device a response to said request to add an item based on a result of said comparison, the response including an indication of whether said current total value of said property inventory exceeds one or more of said plurality of insurance coverage rules and whether said location information is within the at least a first geographical limit.
2. The computer system of claim 1, further comprising program instructions for execution by the processor to receive, from a user operating a mobile device, a request to create a new property inventory, wherein said request to add at least a first item is a request to add said at least a first item to said new property inventory.
3. The computer system of claim 1, wherein said information identifying said at least first item further comprises: an item type and a date acquired.
4. The computer system of claim 1, further comprising program instructions for execution by said processor to receive, from at least one of a user operating said mobile device and a retailer, information identifying a value of said at least first item.
5. The computer system of claim 1, wherein said first image is a still image captured using a camera of said mobile device.
6. The computer system of claim 1, wherein said first image is a video image including a plurality of images of a plurality of items, said program instructions further comprising program instructions for execution by the computer processor to analyze said video image to extract data associated with each of said plurality of items.
7. The computer system of claim 1, wherein said insurance rules include at least one of a coverage rule and an exclusion rule.
8. The computer system of claim 1, wherein said program instructions to analyze said property inventory further comprise program instructions to:
   obtain a value of at least a first item of said property inventory using a third party data source.
9. The computer system of claim 8, wherein said program instructions to obtain a value of at least a first item further comprise program instructions to:
   retrieve a purchase price of said at least first item from a third party database.
10. The computer system of claim 9, wherein said third party database is a database of financial transactions made by said user.
11. The computer system of claim 1, wherein said plurality of insurance rules includes a rule specifying a threshold to determine when a message is to be transmitted to said user indicating that said user has insufficient coverage.
12. The computer system of claim 1, wherein said plurality of insurance rules includes a rule specifying a threshold to determine when a message is to be transmitted to said user indicating that said user has excess coverage.
13. The computer system of claim 1, wherein the data received from the mobile device further comprises temperature data, said data defining a plurality of insurance coverage rules further comprises an insurance coverage rule that at least one of a room and a product be kept at a certain minimum temperature, and said instructions are further for said computer processor to compare said received temperature data to said insurance coverage rule that at least one of a room and a product be kept at a certain minimum temperature.
14. The computer system of claim 1, wherein the mobile device being configured to execute an application program to capture an image of a first item comprises the mobile device being configured to capture video images of a plurality of items, identifying the images using image processing, and geotagging the images.
15. A portable wireless communication device, comprising:
   a communication port;
   a sensor for determining quality of items;
   a processor;
   a memory;

and a program, wherein the program is stored in the memory and configured to be executed by the processor, the program including:

instructions for detecting a user action to add an item to an insurance inventory of said user;

instructions for receiving information identifying an item, including an item type and a date acquired;

instructions for activating a sensor, coupled to the portable wireless communication device, for determining quality of an item, to determine quality of the first item, and for performing an analysis based on data from the sensor;

instructions for: prompting a user to capture, via a camera of the mobile device, an image of one or more of a bar code, serial number or product code of the first item; receive in response to the prompt an image of one or more of a bar code, serial number or product code of the first item; and communicate with one or more comparison services to obtain comparative pricing information associated with the first item employing the at least one of bar code, serial number or product code, instructions for capturing at least a first image of said item and associating said at least first image with a timestamp and geocode data based on a location of said capturing from a GPS receiver of said portable wireless communication device;

instructions for transmitting a request to add said item to a remote insurance processing system, said request including information identifying said user, said item type, said date acquired, said at least first image of said item, said time stamp, said geocode data, the image of one or more of a bar code, serial number or product code of the first item, the obtained comparative pricing information, a result of the analysis and data received from said sensor relating to said item; and instructions for receiving a response from said remote insurance processing system, said response including information based on a comparison of said geocode data and at least a first insurance policy coverage rule specifying a geographical coverage limitation associated with an insurance policy of said user, and responsive to receipt of said response, automatically displaying said response on an interface of said device.

16. The portable wireless communication device of claim 15, further comprising instructions for capturing an image of a purchase receipt associated with a purchase of said item and converting said image to purchase data including a purchase price, a purchase date and a merchant, wherein said request to add said item further comprises information identifying said purchase price, said purchase date, and said merchant.

17. The portable wireless communication device of claim 15, wherein said response from said remote insurance processing system is based on the application of other insurance processing rule associated with the insurance policy of said user.

18. The portable wireless communication device of claim 15, further comprising a touch-sensitive display screen.

19. The device of claim 15, further comprising instructions for receiving information about the item from an inventory system of a retailer and the instructions for transmitting further comprising transmitting the information about the item received from the inventory system of the retailer.

20. A computerized data processing method, comprising:

by a mobile device, coupled to a sensor for determining quality of items, executing an application program to capture an image of a first item, generate an interface prompting a user for data relating to the first item, activate a sensor to determine quality of the first item, perform an analysis based on data from the sensor, prompt the user to capture, via a camera of the mobile device, an image of one or more of a bar code, serial number or product code of the first item, receive in response to the prompt an image of one or more of a bar code, serial number or product code of the first item, communicate with one or more comparison services to obtain comparative pricing information associated with the first item employing the at least one of bar code, serial number or product code, and automatically transmit a record including the captured image data, data entered via the user interface, location information automatically captured via a GPS receiver of the mobile device, time information, the image of one or more of a bar code, serial number or product code of the first item, the obtained comparative pricing information, a result of the analysis, and quality data received from the sensor; and further executing the application program to, responsive to receipt of a response to a request to add an item, automatically display the received response on an interface of the mobile device;

receiving, from a mobile device, a request to update a status of an item of property in an insurance inventory associated with a commercial insurance policy, said request including at least one of (i) information identifying said item as an item to be added to said insurance inventory and including at least a first image of said item and information identifying a geographical location of said item based on information received via a GPS receiver of the mobile device, and (ii) information identifying said item as an item to be removed from said insurance inventory;

updating an inventory system in response to said request to update a status of said item of property in said insurance inventory associated with said commercial insurance policy, said updating including computing a total current value of said insurance inventory in response to said request to update;

operating a coverage engine to compare coverage limits associated with said commercial insurance policy to said total current value of said insurance inventory and said information identifying a geographical location of said item to determine if said total current value is within a coverage limit of said commercial insurance policy and if said geographical location of said item is within at least a first geographical limit of said commercial insurance policy; and transmitting a response to said mobile device based on said determination.

21. The computerized data processing method of claim 20, further comprising:

receiving, from a merchant associated with a sale of said new item of property to said user, information identifying a price of said new item.

22. The computerized data processing system of claim 21, wherein said receiving from a merchant further comprises receiving information identifying a serial number of said new item.

23. The computerized data processing method of claim 20, wherein said insurance policy is a commercial policy and said new item is at least one of an item of inventory and an item of equipment.

* * * * *

UNITED STATES PATENT AND TRADEMARK OFFICE
CERTIFICATE OF CORRECTION

PATENT NO. : 9,836,793 B2
APPLICATION NO. : 12/877784
DATED : December 5, 2017
INVENTOR(S) : Keven J. Busque et al.

It is certified that error appears in the above-identified patent and that said Letters Patent is hereby corrected as shown below:

On the Title Page

Item (75), the first name of the first inventor is incorrectly spelled. The correct spelling is Keven.

Signed and Sealed this
Twenty-fourth Day of April, 2018

Andrei Iancu
*Director of the United States Patent and Trademark Office*